United States Patent [19]

Smith et al.

[11] Patent Number: 5,681,593

[45] Date of Patent: *Oct. 28, 1997

[54] METHOD AND COMPOSITION FOR TREATING PSORIASIS, SEBORRHEIC DERMATITIS AND ECZEMA

[76] Inventors: Steven A. Smith; Lorraine J. Smith, both of 5801 E. 41st St., Suite 420, Tulsa, Okla. 74135

[*] Notice: The term of this patent shall not extend beyond the expiration date of Pat. No. 5,433,957.

[21] Appl. No.: 503,696

[22] Filed: Jul. 18, 1995

Related U.S. Application Data

[63] Continuation-in-part of Ser. No. 985,610, Dec. 3, 1992, Pat. No. 5,433,954, which is a continuation of Ser. No. 518,170, May 1, 1990, Pat. No. 5,171,581.

[51] Int. Cl.$^6$ .......................... A61K 33/24; A61K 31/28
[52] U.S. Cl. .......................... 424/646; 424/617; 424/404; 424/723; 514/192; 514/250; 514/501; 514/861; 420/441; 423/493
[58] Field of Search .......................... 424/646, 617.404, 424/723; 514/501, 863, 192, 250, 861; 420/441; 423/493

[56] References Cited

U.S. PATENT DOCUMENTS

| | | | |
|---|---|---|---|
| 5,171,581 | 12/1992 | Smith et al. | 424/617 |
| 5,433,954 | 7/1995 | Smith et al. | 424/646 |

OTHER PUBLICATIONS

Soter, et al., "Cutaneous changes in disorders of altered reactivity: eczematous dermatitis; Introduction and Classification", *Dermatology In General Medicine*, 2nd Ed., Chapter 58, pp. 507–509, 1979.

Brauner, "Miscellaneous disorders arising in the Skin: Seborrheic Dermatitis", *Dermatology in General Medicine*, 2nd Ed., Chapter 91, pp. 803–807, 1979.

"Seborrheic Dermatitis", American Academy of Dermatology, revised 1993.

Sjovall, et al., "Oral Hyposensitization in Nickel Allergy", J. Amer. Acad. Dermatitis, V. 17, No. 5, Part 1, Nov. 1987.

Gawkrodger, et al., "Nickel Dermatitis: The Reaction to Oral Nickel Challenge," Brit. J. Dermat., 115, pp. 33–38 (1986).

DaCosta, J.M., "Observations on the Salts of Nickel, Especially the Bromide of Nickel", The Medical News, vol. XLIII, No. 13 (1883).

Jordan, W., "Nickel Feeding in Nickel-Sensitive Patients with Hand Eczema", J. Am. Acad. Dermatol., vol. 1, No. 6 (1979).

Kolipinski, L., 4, Monthly Cyclopaedia & Medical Bulletin, pp. 348–355, "On the Uses of Nickel Sulphate in Medicine", 1911.

The Merck Index, Windholz (editor), 10th edition, Merck & Co., Rahway N.J., 1983, p. 932.

Weingartner et al, "Composition of the First . . . in conc. Aqueous $NiCl_2$ and $NiBr_2$ Solutions", J. Chem. Soc. Faraday Trans., 1, 75(12), 2700–2711, 1978.

*Primary Examiner*—Richard L. Raymond
*Assistant Examiner*—Brian G. Bembenick
*Attorney, Agent, or Firm*—Steinberg, Raskin & Davidson, P.C.

[57] ABSTRACT

Psoriasis, seborrheic dermatitis and eczema are treated by oral administration of inorganic nickel compound(s), with or without inorganic bromide(s). In an especially preferred embodiment, the nickel compound used to treat these diseases is $NiBr_2$.

20 Claims, No Drawings

5,681,593

1

METHOD AND COMPOSITION FOR TREATING PSORIASIS, SEBORRHEIC DERMATITIS AND ECZEMA

This application is a continuation-in-part of U.S. Ser. No. 07/985,610, filed Dec. 3, 1992, now U.S. Pat. No. 5,433,954, which is a continuation-in-part of U.S. Ser. No. 07/518,170 filed May 1, 1990, now U.S. Pat. No. 5,171,581.

BACKGROUND OF THE INVENTION

Psoriasis is a chronic skin disorder that is proliferative in nature and widespread throughout the world, afflicting millions of humans and even domesticated animals having similar proliferative integument problems. The skin disorder is characterized by recurrent, elevated red lesions, plaques or rarely pustules on the skin. These plaques are the results of an excessively rapid growth and shedding of epidermal (skin) cells.

No one knows what causes this abnormal cell proliferation. Its severity and course vary greatly from case to case, and also in the individual afflicted with the disease. Recurrences are almost the rule with intervals varying from one month to many years. One person may go through life with a single patch on the elbow, knee or scalp, while another will have repeated attacks of a generalized eruption or widespread chronic lesions lasting for years without remission. As discouraging as it may be, medical science and literature are replete with indications that patients exhibiting such lesions are destined for life to be "psoriatic." With all of the advances in medical science, no one knows what causes this abnormal cell proliferation. With some of it, it is felt that some type of biochemical stimulus triggers this abnormal cell growth. It is still unknown whether the origin of this biochemical malfunction resides in the skin, in the immune system, in the white blood cells, or is possibly psychoneural. It is known that certain environmental factors can "trigger" the initial appearance or worsening of psoriasis. Conversely, the symptoms can spontaneously clear for reasons scientists do not understand. Treatment of the psoriasis is aimed at clearing the lesions for as long as possible. This is what is meant by the term "remission" or "clearance." In any event, medical science has fairly well agreed that psoriasis is an heritable disease in which the specific defect seems to be unknown.

For years there have been many attempts to treat the disease, and several topical and systemic treatments for psoriasis which inhibit cell division have been with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, but recurrences are likely. There is a tendency for each remedy gradually to lose its effectiveness or develop dangerous accumulative toxicity. Rarely, however, is the disease apparently cured, showing no evidence for years.

In the treatment of the disease, medical science has suggested low fat or low protein diets. Drugs such as systemic corticosteroids and ACTH are effective but limited to patients who are in great distress and do not respond to other measures. Such drugs may produce dangerous side effects; and in some instances, once the drugs are discontinued, the eruption may show a marked exacerbation. Folic acid antagonists have been found to have some beneficial treatment but are a dangerous form of therapy. Although other drugs have been suggested, for the most part the serious side effects associated therewith have not made them successful. Ionizing radiation therapy, e.g. grenz-ray treatment, has provided only temporary benefit, but the danger(s) of addiction to such radiation producing radiodermatitis and subsequent carcinoma is not worth continued treatment. Corticosteroid ointment in combination with polyethylene film has had some success, but systemic effects may be caused by extensive use. Ointments have been found to be more beneficial than lotions. A typical ointment may contain anthralin or tar. Hydrophilic ointment containing salicylic acid and sulfur is also found to be beneficial, especially for scalp treatment. Here again, the side effects and the absorption within the human system of these chemicals must be guarded. Other treatments including sunlight baths or ultraviolet (UV) baths with the lesions painted with a solution of coal tar, anthralin or psoralens have been found to be helpful.

Ongoing studies in the art concern the use of vitamin $D_3$ (1,25-dihydroxyvitamin $D_3$). Etretin and Etretinate are new generation retinoids presently being studies for treating psoriasis. Rut again, the side effects must be carefully monitored.

Other ongoing studies include the use of the drug cyclosporine, RS 53179 (a non-steroidal, anti-inflammatory drug), fish oil, hypothermia, and anti-yeast agents.

One method for alleviating psoriasis is taught in U.S. Pat. No. 4,181,725 which teaches a pharmaceutical compound which contains as its active components at least one compound selected from the group consisting of parabromophenacyl bromide, alpha tocopherol, mepacrine, chloroquine, hydroxychloroquine, dibucaine, tetracaine, lidocaine, butacaine, procaine, ethylene diamine tetra, acetic acid, and ethylene glycol bis ($\beta$ amino ethyl ether) -N-N'tetracetic acid within a suitable carrier.

Seborrheic dermatitis (seborrhea) in the least severe form, but most common, is simple dandruff. It can become more severe and form scaly, red patches on the face, ears, chest, and other widespread areas. It often coexists with psoriasis, and many subjects have overlapping features termed "seborrhiasis." Therefore, a continuum may exist whereby these are on the same disease spectrum. Treatments are similar to those currently used for psoriasis, although lower dosages are usually sufficient to control seborrheic dermatitis.

Eczema (including but not limited to atopic, nummular and hand types) often has similar overlapping features with psoriasis. See, e.g., H. Roenigk, Jr. et al., "Psoriasis", ©1991, Marcel Dekker, Inc., Chapter 2. For instance, it is often difficult to distinguish based on clinical appearance. They can coexist, or the disease can begin as eczema and over time turn to psoriasis. Again, treatments are similar with corticosteroids and tar preparations commonly employed for both of these conditions.

Similar conditions to both seborrheic dermatitis and eczema also occur in various domestic animals (mange, etc.). The current invention is felt to encompass all similarly involved species.

Seborrheic dermatitis and eczema have several other features in common with psoriasis. They are very common in the general population. They have no known cause, although many theories are advanced. They have no known cure, although many similar temporary remedies are known. All of these conditions are known to worsen with stress. Finally, there seems to be a hereditary basis or tendency for development of each of these skin disease, although this is not a strict finding.

SUMMARY OF THE INVENTION

The present invention is directed to and encompasses as its object to provide methods and compositions for the topical, oral, or intravenous treatment of psoriasis, seborrheic dermatitis and eczema (including but not restricted to atopic, nummular and hand types). The treatment of other diseases such as primary irritant contact dermatitis, allergic contact dermatitis, lamellar ichthyosis, epidermolytic hyperkeratosis, and certain forms of dermatitis and mange in domesticated animals and psoriatic arthritis are also intended to be encompassed by the appended claims.

It is believed that there is/are specific defective enzyme(s) in humans that is/are genetically predisposed to psoriasis, seborrheic dermatitis and eczema. Certain exacerbating factors (lithium, stress, etc.) interfere with the function of such enzyme(s). It is believed this leads to a buildup of a metabolically active "psoriasis molecule(s)" which in turn either directly or indirectly triggers inflammation in the skin and/or joints. It is believed that the hematopoietic system (especially leukocytes) is the most likely source and most prolific producer of the "psoriasis molecules." A hepatic enzyme(s) probably compounds the problem by failing to catabolize and/or excrete this molecule(s). A defective kidney enzyme(s) may also play a role.

Specifically, this invention proposes and has for its single compound and/or separately and/or oral processes which favorably affect the aforementioned enzyme(s) in people predisposed to psoriasis, seborrheic dermatitis and eczema. Pharmaceutically acceptable inorganic nickel compound(s) with or without accompanying inorganic bromide(s) are administered to diseased subjects over time with alleviation of the signs and symptoms of the disease(s).

The exact mechanism of this beneficial action on these diseases is not well understood at this time. It is felt, however, that nickel-dependent metalloenzymes are partially defective in diseased subjects, thus requiring additional nickel for greater efficiency of action and consequent improvement in the diseased condition. This hypothesis is not meant to limit the scope of the claims in any manner whatsoever.

More particularly, the present invention is related to a method of treating human beings for psoriasis, seborrheic dermatitis and eczema comprising the step of orally administering an effective amount of a disease-inhibiting formulation containing a non-toxic, pharmaceutically acceptable nickel (Ni) salt(s) in a human patient, and dosing the patient such that said formulation provides an amount of nickel from about 2 to about 300 mcg/kg (micrograms per kilogram) of patient weight/day is administered. In a preferred embodiment, the nickel salt is $NiBr_2$, $NiSO_4$, $NiCl_2$, mixtures of any of the foregoing, etc. In an especially preferred embodiment, the nickel salt is nickel bromide ($NiBr_2$).

The present invention is also related to a composition for treating psoriasis, seborrheic dermatitis and eczema in human beings comprising nickel (Ni) in an amount from about 2 to about 300 mcg/kg of patient weight/day, the dosage of Ni being derived from a non-toxic pharmaceutically acceptable Ni salt(s). The composition may be in any pharmaceutically acceptable form for oral administration, including liquid, capsule, and tablet form.

In a preferred embodiment, the dosage of said Ni is present in an amount for treatment within the range of from about 5 to about 150 mcg/kg of patient weight/day. In other preferred embodiments, nickel is orally administered in an amount from about 5 to about 50 mcg/kg of patient weight/day.

DETAILED DESCRIPTION AND EXAMPLES

A human tissue cell membrane, such as a liver cell or hepatocyte, contains certain sub-cellular organelles which are specialized parts of a protozoan or tissue cell. These subcellular units include mitochondria, the Golgi apparatus, cell center and centrioles, granular and agranular endoplasmic reticulum, vacuoles, microsomes, lysosomes, plasma membrane, and certain fibrils, as well as plastids of plant cells. Leukocytes and perhaps other rapidly dividing cells are believed to be the primary site of production of the "psoriasis molecule" (P.M.). Hence it is an object of this invention to biochemically and/or genetically change or reduce the effect of this hideous disease by treating the affected sub-cellular organelles with compounds of nickel and bromide. The key to the invention is to effect transport of the element nickel (Ni) into the cell and sub-cells, such as the mitochondria or Golgi wherein the needful metalloenzymes can catabolize P.M. into a less toxic and/or easier excreted molecule. It is believed the rejection of nickel from the cell prevents a biochemical change in the P.M. to a less toxic form. It is believed that the use of Br with Ni is an effective carrier to overcome this rejection. The P.M. may then be changed to a less toxic catabolic product by treatment of a nickel dependent metalloenzyme located in the sub-cellular organelles. The nickel (Ni)/bromide (Br) of the invention may become a "catalytic lever" or "switch" to activate the metalloenzyme to its maximum function. This hypothesis is provided for discussion purposes only, and is not meant to limit the appended claims in any manner whatsoever.

Since the exact etiologies of these diseases are not known, one cannot pinpoint the exact beneficial mechanism of action of this invention. However, the inventors believe that there exists an inherited enzymatic defect in diseased individuals that leads to a buildup of a metabolic substrate that triggers a cascade of immunologic mechanisms that causes disease manifestation.

It is believed that this defective enzyme is a nickel-dependent metalloenzyme, and that supplying it with additional nickel can assist in the general efficiency of this enzyme's function. Thereby, the above-mentioned metabolic substrate can be more easily converted into a less toxic and/or more easily excretable metabolic product.

The bromide(s) role is not fully understood at this time, but it seems to be one of facilitator, either through physiological assistance in nickel transport, absorption, or some more direct enzymatic action. Bromide is not felt to be an absolute requirement for utility of this invention but may be required for greater safety and greater effectiveness.

One form of the invention is directed to the topical or oral use of nickel dibromide ($NiBr_2$) or $NiBr_2$ hydrate in adult dosages within the range of 0.037 mg to 370 mg $NiBr_2$ per dose. As such, this is equivalent to the use of 0.01 mg to 100 mg of Ni per dose. The dosages can be mixed in sucrose or lactose or other appropriate form and can be contained within a gelatin capsule or other appropriate oral vehicle. With children, the pediatric dosage is 0.001 mg to 10 mg of $NiBr_2$ per kg per dose within purified or distilled water plus any form of pleasant-tasting flavoring (elixir). The dosages can be available for a variety of situations, including from once a week or once a month to once or twice daily dosages. In some instances, once a day for 5 to 15 days per month for up to 6 months may be effective. It may be desirable or necessary to provide bromide preloading and/or post loading wherein 5 to 500 mg of bromide would be given orally (p.o.) in capsule or elixir in a form such as sodium bromide, potassium bromide, or ammonium bromide or combinations of these which would be given in dosages once daily from 5 to 15 days prior to or after the dosing of $NiBr_2$. In other instances, bromide formulations may be given simultaneously with the $NiB_2$.

Another process for treatment would include first obtaining a nickel patch test of a patient to determine if there is any contact allergy. To determine effectiveness, pre-treatment color photographs of the psoriasis lesions would be obtained prior to starting. Also, pre-treatment color photographs of the psoriasis lesions would be obtained prior to starting. Also, pre-treatment serum tests for nickel, bromide, zinc and copper, a complete blood count (CBC), and a sequential multichannel autoanalyzer count (SMAC) would be accomplished. A 90 kg man would ingest 2 mg of nickel as nickel sulfate ($NiSO_4$) and 20 mg of bromide (Br as sodium bromide (NaBr) per day. These are mixed together in 15 cc of distilled or purified water and taken once daily p.o. on an empty stomach. This process would be repeated for 21 days. Subsequently, a nickel patch test would be taken at a three-week anniversary, photographs taken weekly after starting the process, and post-treatment serum tests as identified in the pre-treatment tests are repeated.

References and studies indicate that the use of NaBr is within well-recognized safe limits. For example, if 20 mg of bromide by way of NaBr were given orally once a day for 21 days, it would be equivalent to 420 mg given assuming 100 percent (100% absorption and an acceptable daily intake (A.D.I.) were 0.4 mg/kg/day. Thus, for a 90 kg adult male, 20 mg of bromide per day is well under the A.D.I. or 35 mg per day. Reference is made to Van Leeuwen, F. X. et al., The Toxicology of Bromide; *CRC Critical Reviews in Toxicology,* 18:189–213; (1987). This reference indicates that the dietary intake in the United Kingdom and in the Netherlands is within the range of 2–17 mg per day. There are apparently no studies on the carcinogenicity. Bromide has been given for 140 years without any carcinogenic effect being reported. See Livingston S. et al.; Bromides in the Treatment of Epilepsy in Children; *American Journal of Diseases of Children;* 86:717–720; (1953). Likewise, the literature indicates that the quantitative exposure giving a 90 kg adult male 2 mg nickel (Ni) by way of $NiSO_4$—$6H_2O$ orally and daily for 21 days will equal 42 mg given. This daily dose is approximately two times higher than that recommended for contaminated IV fluids per day and twenty percent (20%) of dose causing increased coronary artery resistance in single IV dose in dogs. Assume five percent (5%) of the nickel absorbed would equate to 2.1 mg. Assuming thirty percent (30%) of that which is absorbed is deposited in tissues for a mean retention time of 200 days, 30 micrograms (0.3×100) retained each day for the 21 days would equate to a total of 630 micrograms retained. If the normal body burden of Ni equals 7 micrograms per kg, therefore, approximately 21 days will be required to double body burden of Ni for a 90 kg adult. Reference is made to Sunderman, F. W., Sr.; Potential Toxicity from Nickel Contamination of IV Fluids. Soluble nickel salts such as nickel chloride, nickel sulfate, and nickel ammoniumsulfate, have not been shown to be carcinogenic; Sunderman, F. W. Sr.; A Review of the Metabolism and Toxicology of Nickel; *Annals of Clinical and Laboratory Science;* 7:377–398; (1977).

Hence, based on the literature and the studies, it would appear that the use of nickel sulfate and sodium bromide can be effectively employed. The bromide may be absorbed topically from bath solutions or other formulations in creams, ointments, or lotions.

An exemplary test includes two psoriatic patients with active skin disease and a healthy control. The test subjects will be immersed in water high in bromide content. The water of the Dead Sea is found to be of that quality. The subject would be immersed, neck down, for 30 minutes every hour for two four-hour sessions daily for a total of ten days. All activities, including bathing, will be done in sun-shaded facilities, and no suntanning will be permitted. Prior to the study, nickel patch testing as above-described is done on all the subjects, and no medications of any type (systemic of topical) will be taken for at least six weeks prior to the study, during the study, and for six weeks after the study. Only bland emollients will be permitted. Nickel sulfate containing 2.5 mg of nickel is administered orally twice daily during the ten-day study at the beginning of each four-hour bathing session. The aforesaid serum and urine level tests for bromide and nickel will be obtained from all test subjects prior to the onset of each treatment day and at the end of the treatment period with similar levels being tested at the end of each week after therapy. The CBC, SMAC, serum zinc, and serum copper levels will be studied at the beginning and the end of the treatment period and at the end of the study, followed by a nickel patch test.

DETAILED DESCRIPTION OF PREFERRED EMBODIMENTS

The following examples illustrate various aspects of the present invention. They are not to be construed to limit the claims in any manner whatsoever.

EXAMPLE 1

A preliminary study was conducted in conjunction with a 39 year old white male who had over a 15-year history of difficulty controlling the plaque-type of psoriasis vulgaris. The patient had been treated for approximately five years previously with limited success, with maximum b range ultraviolet rays (UVB), along with topically applied tar, corticosteroids, and 5-fluorouracil. The history of the patient showed active flaring of the plaque type of psoriasis over 20 to 30% of the body surface area which were scaly and thickened. No pustules nor inverse patterns were noted. There was minimal involvement of the disease on the face, and the palms of the hands were spared.

Prior to treatment, the following evaluations were conducted: nickel patch testing, exercise tolerance testing, serum nickel, bromide, zinc, copper, SMAC, blood CBC drawn, and preliminary photographs of the affected areas were taken.

The solution itself was obtained by mixing together nickel sulfate ($NiSO_4$)•$6H_2O$ and sodium bromide. Nickel dibromide ($NiBr_2$) resulted in a 5 mg/50 mg ratio of Ni to Br. These were mixed together in purified water to a concentration of 2 mg of Ni and 20 mg of Br per 15 cc of solution. These compounds mixed easily into a colorless solution and were placed in a standard, round, glass pharmacy jar. The compound minerals themselves were ASC grade and purchased from New York City Chemical Corporation. The study comprised the patients' ingestion of very small amounts of the subject solution in order to effect ingestion of 2 mg of nickel and 20 mg of bromide once daily for 21 days. Every seven days standard photos were taken; and on day 21, laboratory tests of serum, nickel, bromide, zinc, copper, SMAC, and blood CBC were conducted. The ingestion by the patient was to be conducted on an empty stomach. Following the treatment, a nickel patch test was conducted along with standard photographs at one-week, three-week, and five-week intervals, with tests for serum nickel and bromide at three weeks post treatment.

During the three-week course of therapy, the following results were noted:

1. No new psoriatic lesions (plaques) were noted at one week and two weeks into therapy. There was a very rare new papule noted at three weeks into therapy. This is a positive result, especially when considered in the setting of rapidly flaring disease prior to the initiation of this treatment and since this patient was in the midst of some severe domestic stresses during the treatment period. Stress has been considered a factor in triggering psoriasis lesions.

2. The existing lesions became less scaly and less reddened and thinner during the entire treatment course. The periphery (circumference) enlarged minimally, and small areas of more normal appearing skin appeared in their centers during treatment.

3. One area on the central chest showed more pronounced clearing than any of the rest of the lesions. There was approximately 50% complete clearing in this area.

At three weeks post-treatment, i.e. the patient was completely off treatment for three weeks, there was noticeable worsening on all the above parameters (new lesions forming, existing lesions turning more bright red in color and producing more bothersome scaly buildup, and all lesions thickening notably).

The above findings are felt to reflect favorable effects of the study medication on the test patient's skin.

Modifications

Although certain specific forms of nickel and bromide compounds are set forth herein, other pharmaceutically acceptable compounds are inclusive of the invention, e.g. nickel sulfate ($NiSO_4$), nickel chloride ($NiCl_2$) sodium bromide (NaBr), potassium bromide (KBr) and ammonium bromide ($NH_4Br$).

In many instances pre, during, and/or post treatment will include topical and/or systemic (oral) or intravenous use of anti-bacterial compounds, e.g. penicillin, and anti-fungal agents, e.g. Ketoconazole.

EXAMPLE 2

In vivo studies have been made to investigate the effects of a nickel bromide oral solution therapy for an individual with psoriasis. Details of these studies and their positive results are as follows.

There were three phases to a first clinical study of an adult 41 year old male including Pre-Treatment, Treatment, and Post-Treatment. The test subject was selected due to long-standing treatment-resistant plaque-type psoriasis vulgaris. He was also very ready to try new and innovative therapies. Informed consent was obtained.

During the Pre-Treatment Phase various baseline laboratory studies were obtained including skin and throat cultures and routine hematology and blood chemistries. Blood levels of nickel, bromide, copper, and zinc were documented. Standard whole body and close-up clinical 'before' photographs were also obtained. A two week course of antibiotics Pen VK 500 mg qid, Rifampin 600 mg qd, and Nizoral 400 mg qd (antifungal) was given the patient. This permitted study of the effects of such antibiotics.

The Treatment Phase consisted of daily oral administration of nickel dibromide aqueous solution in dosages ranging from 2–50 micrograms (mcg) of Ni/kg of patient weight/day. Standard photographs, as well as blood testing similar to the Pre-Treatment regimen, were obtained. Standard clinical assessments were also documented at all phases.

Post-Treatment Phase included all of the above-mentioned blood tests and standard photographs as well as standard nickel cutaneous patch testing.

Test Article and Vehicle

Chemical grade nickel di-bromide was obtained from New York City Chemical Company. This was carefully weighed on an analytical scale and was mixed with appropriate volumes of purified and distilled water. This was readily soluble and stored in a brown pharmacy bottle. All appropriate chemistry calculations were taken to assure accurate concentration and dosing.

Study Course

Daily dosing was accomplished by the test subject measuring a pre-defined amount of test medication into a graduated dose cup. Daily dosing was taken on an empty and fasted stomach.

Results of Clinical Observations

During the first 10 weeks of therapy, the patient had approximately 95% clearing of total body psoriasis lesions based on clinical examinations and serial clinical photographs. Nickel di-bromide aqueous solution was given orally at very low doses. Notable improvement of toenail psoriasis was documented. The average nickel dose during the first 10 weeks of therapy was 12.5 mcg/kg/day which was equivalent to 50 mcg/kg/day of $NiBr_2$. Clinical symptoms of itching and burning of the skin were improved within one week of starting therapy. Notable improvements of skin lesions were documented and photographed within two weeks of starting therapy. These improvements consisted of thinning psoriasis plaques as well as loss of scale and fading of the degree of erythema (inflammatory redness of the skin).

In the following seven weeks the average nickel dosage was reduced to 4.6 mcg/kg/day (equivalent to 18.4 mcg/kg/day of $NiBr_2$). There was a slow reappearance of the symptoms and a possible worsening of some of the existing psoriasis lesions.

Overall, patient acceptance of the medication was high, and at the end of the therapy the patient wished to continue taking it even though it had to be discontinued due to the study design.

EXAMPLE 3

A subsequent study was conducted with a variety of patients with certain selection criteria as follows: (1) They had to be in good health and on no medications; (2) They had to be between the ages of 18–58 years old; (3) Women needed to have no child-bearing capacity; (4) Patients needed to weigh between 40–100 kg; (5) Patients needed to have no known industrial exposure to nickel or pharmaceutical/other exposure to bromides; (6) They needed to have reasonably normal renal and hepatic function on routine blood testing; and (7) They needed to discontinue all preexisting medications for at least two weeks prior to the study. Subjects were allowed to maintain bland emollients during the study, however, no prescription or even over-the-counter medications were allowed other than the test article.

There were three phases to this study including Pre-Treatment, Treatment, and Post-Treatment.

During the Pre-Treatment Phase (week 0), various baseline tests were conducted. These consisted of routine hematology and serum chemistry as well as blood testing for nickel, bromide, zinc, and copper. A routine patch test for nickel was also conducted prior to the study and then repeated at the end of therapy (See Post-Treatment phase below). Clinical history and examinations were obtained as well. All patients had routine stable and/or flaring plaque-type psoriasis vulgaris. All patients had classic cases with no question regarding the diagnosis. All patients gave their voluntary consent to participate in this study. Standard whole body and close-up clinical photographs of selected regional areas were also obtained.

The treatment phase consisted of daily oral administration of nickel di-bromide aqueous solution. The dose for all patients was standardized to 10 mcg/kg/day of nickel component (equivalent to 40 mcg/kg/day of $NiBr_2$). All of the Pre-Treatment Phase testing was again accomplished at four weeks and eight weeks of treatment. Standard clinical assessments and photographs were also documented at all phases. Treatment was terminated at 8 weeks.

Post-Treatment Phase consisted of four weeks of follow up immediately following the Treatment Phase. All the blood testing done during the Pre-Treatment Phase was again accomplished at the end of the Post-Treatment Phase (12 weeks). This included standard nickel patch testing as well as clinical assessments and standard clinical photographs.

Test Article and Vehicle

Nickel di-bromide powder was obtained from Alfa Inorganics. This was rated as anhydrous and 99% purity. Appropriate amounts of this powder were weighed on an analytical scale and carefully mixed with appropriate volumes of purified and distilled water. This was readily soluble and stored in brown pharmacy bottles. All appropriate chemistry calculations were taken to assure accurate concentration and dosing.

Daily patient dosing was accomplished by the test subject measuring a predefined amount of the test vehicle into a graduated dose cup. This amount was determined by the patient's weight and the Study Design. Daily dosing was taken on an empty and fasted stomach (at least 8 hours after having eaten and at least one hour prior to eating).

Results of Clinical Observations

Five patients were initiated on the study. Four of the patients had no side effects or adverse reactions to the test article/medication (daily oral aqueous solution of nickel di-bromide). One patient had gastrointestinal distress which soon stopped after the medication was discontinued and she was removed from the study. The remaining four patients completed the study without any side effects. Of these, two were men and two were women. The two men both had marked improvements of all skin disease, substantially 95% clearing. Skin parameters followed included erythema, elevation, and scale present on existing plaques.

One of the two women patients improved moderately on treatment with about 35% clearing of the psoriasis. Substantially all of the thin plaques cleared. The thicker sacral and leg plaques did not clear, but their appearance changed during the therapy. The other female patient showed no noticeable improvement. The clinical significance of this is not known. Skin improvements on the three patients occurred between 4–8 weeks during the treatment phase. The patients who noted improvement during the treatment phase also continued to improve during four weeks of post-treatment follow up. The compliance by the four patients was good. Patient acceptance of the medication was also quite good with each of the four patients requesting to stay on the medication. This was not allowed due to the nature of the study. It is believed that there was sufficient marked improvement in a sufficient number of people that indicates that the concepts of the invention as disclosed and claimed will provide some relief from psoriasis lesions.

EXAMPLE 4

A study was performed from September 1991 to March 1992 on one subject with seborrheic dermatitis. This condition had existed for several years and manifested as scaly, itchy scalp. Previous treatments included tar and other medicated shampoos which were required continually for control of this disease.

Once daily oral administration of $NiBr_2$ aqueous solution was given at a dosage of 56 mcg/kg/day (equivalent to 15 mcg/kg/day nickel component) for 19 weeks.

Pre-treatment, treatment and post-treatment evaluations were conducted including regular exams and appropriate laboratory testing (serum chemistry profile, complete blood count profile, serum nickel and bromide, and zinc and copper, and routine urinalysis). Nickel patch testing for cutaneous sensitivity was done at the pre and post-treatment intervals.

Results of this study showed no adverse reactions. All laboratory parameters remained within pre-treatment limits except serum nickel and bromide which elevated appropriately. Efficacy evaluations showed clearance of all signs and symptoms of seborrheic dermatitis after sixteen weeks of treatment. This favorable response persisted for nine months of post-treatment follow up, despite absence of therapy of any type during this interval. This type of remittive therapy is unique compared to existing accepted treatments.

Case Studies in Treating Eczema (Atople Dermatitis) With Nickel and Bromide Salts Clinical case studies were performed on subjects selected from the patient base at the clinic of Dr. Steven A. Smith. Subjects were selected by Dr. Smith on the basis of a history of chronic, refractory eczema with a pattern of only minimal to moderate response to commonly used topical and systemic proscription medications followed by flareups within a few weeks or months. Study medication was prescribed for the subjects as an addition to their preexisting treatment regimen. Objective evaluation criteria used were: changes in body area coverage by the eczema; severity of eczema and any associated skin infections in the areas covered; stability of the disease condition; reduction or increase in types, strengths or amounts of concurrent medications required to control the eczema and, if any, the associated infections. Subjects were also questioned for a subjective evaluation of their disease condition: degree of itchiness, feel of the skin, their perception of improvement or dexioration in their eczema.

Complete charts are maintained on each subjects, with a thorough history of the patient's eczema and its treatment pattern being taken to establish a baseline. Subjects were typically seen for evaluation and adjustment of their medications monthly: more frequently if needed by the patient, less frequently if substantial improvement was being experienced.

Three different formulations of the study medications were used; the bromide originated from potassium bromide and sodium bromide and the nickel from nickel sulfate in an aqueous solution; the nickel and bromide content shown were assayed by the University of Virginia Health Sciences Center Trace Minerals Laboratory:

(1) Formula B consisted of bromide ions at a concentration of 5.0 mg/ml and nickel ions at a concentration of 0.01 mcg/ml; the aqueous solution contained 20% alcohol as a preservative.

(2) Formula E consisted of bromide ions at a concentration of 4.7 mg/ml and nickel ions at a concentration of 0.06 mcg/ml; the solution also contained dilute mounts of potassium sulfate and sodium chloride along with 12% alcohol as a preservative.

(3) Formula 5 consisted of bromide ions at a concentration of 5.2 mg/ml and nickel ions at a concentration of 191 mcg/ml; the aqueous solution contained 20% alcohol as a preservative.

Twelve subjects were recruited for the study starting in December of 1994. No adverse events or side effects were reported by the subjects during the study and none dropped out. Eight subjects exhibited distinct improvement while taking their study medication as compared to their previous condition or disease pattern:

Case No. 1: James B. Is a 140 lb, 45 year old white male with a long history of chronic, severe body eczema with a pattern of only mild to moderate responsiveness to medication followed by flare ups of the eczema. The patient was first seen by Dr. Smith on Feb. 6, 1995 with large parts of his body exhibiting red excoriated lesions with scaling and scabing, diagnosed as severe eczema or atopic dermatitis with pyoderma (skin infection). The patient was treated with systemic prednazone, antibiotics and topical corticosteroids. The patient did moderately well, consistent with his historic pattern.

On February 29 the patient was admitted to the study and started 4 ml daily of Formula B; the antibiotics and topical corticosteroids were continued. The subject was seen again on March 22 and exhibited marked improvement (95% clearing on the upper body with moderate continued improvement on his legs). Some Infection remained, so antibiotics were continued, along with the study medication topical therapy. On April 26 continued rapid improvement was evident, although some skin infection still lingered. On May 25 the subject exhibited 99% clearing on his body, with near normal skin, a condition he had not achieved in many years. Antibiotics were discontintinued, study medication was continued as Formula E, and topical medication was recommended on an as needed, intermittant basis.

Case No. 2: Christopher C. is a 10 yr old, 300 lb., white male with a history of multiple allergy related diseases, including asthma and chronic, extensive body and scalp eczema. Christopher stared as a patient of Dr. Smith in November of 1994; he returned on Apr. 24, 1995 with flaring eczema and skin infection. He was treated with topicals and an antibiotic, to which he exhibited an allergic reaction. On May 1, 1995 he returned, was put on a different antibiotic, continued the topical treatment and was started on the Study with a dose of 10 ml per day of Formula E. He was seen again by Dr. Smith on May 11; his eczema had stabilized. On May 25 he exhibited some improvement in his eczema; his skin infection had cleared, allowing the antibiotic to be discontinued. The Formula E and topicals were continued. On June 15 the subject was evaluated again by Dr. Smith. His body eczema continued to improve over the previous evaluation on May 25, now exhibiting a moderate to marked improvement over the May 1 baseline evaluation when the Formula E was begun. The subject was, however, experiencing a flaring of his scalp eczema which was thought to be due to a new hair wash gel he had started. The Formula E dose was reduced to 8 ml and the subject continued on the study at the time of this report.

Case No. 3: Lulu F is a 6 year old Mexican American female who had been treated at the clinic at various times over a two year period. She had a history of wide spread atopic dermatitis or eczema with frequent pyoderma complications; she had been relatively treatment resistant. On Mar. 30, 1995 she came to the clinic with flaring of her eczema, especially on her arms and legs, and was started on a topical therapy. On April 13 she returned with only minor improvement. She was admitted to the study and started on 2 ml of Formula B along with continuing the topical therapy. She returned for evaluation on June 1. Her eczema appeared much improved over the previous visit; the subject reported her skin felt much better, not as dry. She was continued on the Formula B and topical ointment until the next evaluation.

Case No. 4: Martha M. is a 53 year old, 210 lb white female with severe, life-long eczema. She had been taking prednazone for 3 years to control her eczema in the moderate range; she flared periodically with herpes or staff infections on her skin, requiring antibiotics. In August of 1994 Dr. Smith discontinued the use of systemic prednazone due to the extensive past use and continued topical therapies. In December of 1994 the subject was admitted at the start of the study on 4 ml/day of Formula B and continued on the topical formula. In January of 1995 the subject's was improved; the subjected stated that her eczema was doing better than it had in years; her skin felt better to her, more normal. The subject returned again for evaluation in March, 1995. Her condition was stable with some improvement over the previous visit. The subject's topical therapy was reduced. The subject next returned for evaluation April 25. Her eczema was stable with only diffuse redness. She had minimal infection and no flaring of her disease condition. She was changed to 8 ml of Formula E. At her evaluation on May 16 she was experiencing mild flaring of her eczema with red patches on her arms and some crusted lesions on her legs. On June 20 her body eczema was doing better and her face was doing worse; she had not been using any topical treatment so these were restarted along with antibiotics for mild skin infection. During the 6 months this subject had been on the study medication she reported that the combined mount of medication she was taking was the least in over 3 years while experiencing the lowest overall level of eczema and associated skin infection.

Case No. 5: Rick S. is a 41 year old, 199 lb. white male who first presented himself on Mar. 30, 1995, seeking a "second opinion". He was experiencing a red rash over his entire body, with red, crusty scabed patches on his forearms and elbows, along with skin infections; he reported that he was unable to get out in the sun without exacerbating his rash and itchiness. He was already under medication from another doctor for this condition; from his charts he had been to a number of doctors and had a history of difficult to treat eczema and other skin diseases. As a result of his diagnosis, Dr. Smith altered the patients medication and administered an injection of Kenalog. The patient returned in 7 days for follow-up on April 6 with noticable improvement in his rash, although the rash persisted on his face and the red scaly patches were still present on his hands and forearms. At this time he was admitted to the study and put on 10 ml per day of Formula B, while continuing his other medication. The subject was seen again in 2 weeks on the 19 of April; them was some continuing improvement in his atopic dermatitis/ eczema but the skin infection persisted. His antibiotic therapy was altered along with the topical treatment of the lesions on his forearms. The subject was next evaluated on May 3. Continued improvement was exhibited: his face had cleared except for mild redness; the lesions on his arms had begun healing. His medications were reduced, including Formula B to 8 ml per day. The subject returned for follow-up on May 24. The subject reported that he was doing much better and was now able to work out in the sun without itching developing, which he had not been able to do in over a year. His antibiotic dose was decreased and the dose of Formula B was reduced to 7 ml per day. The subject was evaluated again on June 21. His eczema and sun sensitivity continued in a stable pattern with only minimal improvement over his previous visit. Overall improvement since beginning the study was rated at 70%; the subject reported that his skin had not been as clear in over 4 years.

Case No. 6: Tim O. is an eight year old, (64 lb white male who first came to the clinic on March 14 complaining of severe skin itch. He had multiple red patches with some crusting and peeling on his lower legs and arms; he reported a long history of dry, itchy skin. He was treated with oral antibiotics and topical therapy for his eczema. He returned for follow-up on March 28 with distinct improvement and continued the same therapy. He returned to the clinic on April 28 with his eczema flaring in spite of the therapy. His topical therapy was adjusted, antibiotics were discontinued and he was admitted to the Study with a starting dose of 3 ml per day of Formula B. He returned for follow-up evaluation on June 19. His eczema was much improved (approximately 70 to 80% clearing) and stabilized. His topical therapy was reduced and the Formula B dose reduced to a maintenance level of 2 ml per day.

Case No. 7: Patricia W. has been a patient of Dr. Smith since September of 1992 with chronic eczema characterized by temporary improvement when initially treated followed within 1 to 2 months by a reflaring of the disease. As a part of continuing treatment every eczema therapy suggested by the literature was tried without success; the patient continued to experience regular flaring of her severe eczema with only partial clearing in between episodes. In January of 1995 Patricia W. was admitted to the study and started on a daily dose of 5 ml of Formula B in addition to her regular topical and anti-pruritic therapy. In the first follow-up evaluation on February 19 the subject reported that her skin felt better with less itching. Her topical medication was reduced. On March 3 her eczema continued to improve and itching was reduced. On March 24 her eczema was only moderately better but was stable; the study medication dose was increased to 6 ml daily. At her last evaluation on May 30 her severe eczema had improved by a consistent 50% over the 5 months of treatment with the study medication, but was still a problem for her. The study medication dose was reduced to 5 ml per day. The subject had achieved a greater degree of clearing, was more stable without periodic episodes of flaring disease and required fewer antibiotics and systemics to alleviate her symptom while taking the study medication.

Case No. 8: Gary M. is a 36 year old, 170 lb. white male with a history of difficult to treat dishydrosis or hand eczema. He was first seen by Dr. Smith in August of 1993 and has been treated with intramuscular and oral corticosteroids (kenalog and prednazone) along with topicals and antibiotics for infection complications. He would typically improve for 2 to 4 weeks then his condition would again flare to some degree. He was admitted to the study in December of 1994 with a rash on his face, upper arms, ankles and shoulders; his hand eczema was flaring severly having to withdraw from prednazone as a part of his continuing therapy due to length of time on it. He was put on 8 ml of Formula S per day in addition to continuing topicals and antibiotics. In January his eczema condition was showing minor improvement with no flaring but his infection was worse; antibiotics were adjusted for the recalcitrant infection and Formula S dose was increased to 10 ml per day. In February his eczema was stable to mildly improved and the infection was gone; the oral antibiotic was discontinued and the Formula 3 dose lowered to 6 ml per day. In the March evaluation the subject's body and face rash had substantially cleared and the hand eczema had substantially improved. The subject reported that his eczema was noticably more stable and under control than was customary. April brought continued progress with no flaring; the subject felt that the texture of his hands felt more "normal". In June the subject was experiencing some flaring in his hand eczema which he attributed to working with oil and grease. In general the subject was very pleased with the current state of his chronic eczema, feeling that it was more under control than it had been for a number of years. He was no longer experiencing periodic skin infections due to raw and cracked skin from eczema (no antibiotics for 4 months). Also no systemic corticosteroids, such as kenalog or prednazone, had been required in 6 months to control the eczema.

The examples provided above are not meant to be exclusive. Many other variations of the present invention would be obvious to those skilled in the art, and are contemplated to be within the scope of the appended claims.

What is claimed is:

1. A pharmaceutical formulation for the treatment of eczema in a human patient comprising:

from about 0.01 to about 191 mcg nickel ions/ml and an effective amount of bromide ions to promote the anti-eczematic effect of said nickel ions.

2. The pharmaceutical formulation of claim 1, wherein the concentration of said nickel ions is from about 0.01 to about 0.06 mcg/ml.

3. The pharmaceutical formulation of claim 1, wherein the concentration of said bromide ions is from about 4.7 to about 5.2 mg/ml.

4. The pharmaceutical formulation of claim 1, further comprising a preservative.

5. The pharmaceutical formulation of claim 4, wherein said preservative is selected from the group consisting of alcohol, potassium sulfate, sodium chloride, and mixtures thereof.

6. The pharmaceutical formulation of claim 5, wherein said preservative is alcohol.

7. The pharmaceutical formulation of claim 6, wherein said alcohol is present in an amount from about 12 to about 20% (v/v) of the formulation.

8. The pharmaceutical formulation of claim 5 comprising: about 5.0 mg/ml bromide ions; about 0.01 mcg/ml nickel ions; and about 20% (v/v) alcohol.

9. The pharmaceutical formulation of claim 5 comprising: about 4.7 mg/ml bromide ions; about 0.06 mcg/ml nickel ions; and about 12% (v/v) alcohol.

10. The pharmaceutical of claim 5, comprising about 5.2 mg/ml bromide ions; about 191 mcg/ml nickel ions; and about 20% (v/v) alcohol.

11. The pharmaceutical formulation of claim 1, wherein a unit dose comprises from about 0.02 to about 1910 mcg of said nickel ions.

12. A unit dose of the pharmaceutical formulation of claim 1 comprising from about 2 to about 10 mls said formulation.

13. A pharmaceutical dosage form, comprising from about 0.02 to about 1910 mcg nickel and an effective amount of bromide sufficient to promote the anti-eczematic effect of said nickel.

14. The pharmaceutical dosage form of claim 13, comprising from about 9.4 to about 52 mg of said bromide.

15. An aqueous pharmaceutical formulation comprising from about 0.02 mcg nickel ions and from about 9.4 to about 52 mg bromide ions.

16. A pharmaceutical unit dose comprising pharmaceutically acceptable nickel salt and a pharmaceutically acceptable bromide salt, wherein said dosage form provides from about 0.02 mcg to about 1910 mcg of nickel ions and from about 9.4 to about 52 mg bromide ions when administered to a human patient.

17. A method of treating eczema in a human patient comprising administering from about 2 to about 10 mls of the pharmaceutical formulation of claim 1 to said patient.

18. A method of treating eczema in a human patient comprising administering from about 0.02 to about 1910 mcg nickel/day and from about 9.4 to about 52 mg bromide/day to said patient.

19. The method of claim 18, further comprising administering to said patient an active agent selected from the group consisting of a topical corticosteroid, a systemic corticosteroid, and antibiotic or a combination thereof.

20. The pharmaceutical formulation of claim 1, wherein said nickel ions are provided by nickel bromide.

* * * * *

UNITED STATES PATENT AND TRADEMARK OFFICE
CERTIFICATE OF CORRECTION

PATENT NO. : 5,681,593

DATED : October 28, 1997

INVENTOR(S) : Steven A. Smith and Lorraine J. Smith

It is certified that error appears in the above-identified patent and that said Letters Patent is hereby corrected as shown below:

On the cover page, at item [76], [*] Notice, delete "5,433,957"

and replace with --5,433,954--.

Signed and Sealed this

Twentieth Day of January, 1998

Attest:

BRUCE LEHMAN

*Attesting Officer*   *Commissioner of Patents and Trademarks*